(12) United States Patent
Samuels et al.

(10) Patent No.: US 6,925,317 B1
(45) Date of Patent: Aug. 2, 2005

(54) INTEGRATED ALIGNMENT DEVICES, SYSTEM, AND METHODS FOR EFFICIENT FLUID EXTRACTION, SUBSTANCE DELIVERY AND OTHER APPLICATIONS

(75) Inventors: Mark A. Samuels, Norcross, GA (US); Krishna S. Kumar, Duluth, GA (US); Garrett T. Robinson, Atlanta, GA (US); J. David Farquhar, Commerce, GA (US); Allison Minton, Atlanta, GA (US); Diedre Williams, Atlanta, GA (US); Michael R. Hatch, Sugar Hill, GA (US); Alan M. Smith, Atlanta, GA (US); Teresa Woods, Atlanta, GA (US); Mark Vreeke, Houston, TX (US)

(73) Assignee: SpectRx, Inc., Norcross, GA (US)

( * ) Notice: Subject to any disclaimer, the term of this patent is extended or adjusted under 35 U.S.C. 154(b) by 49 days.

(21) Appl. No.: 10/018,001

(22) PCT Filed: Jun. 12, 2000

(86) PCT No.: PCT/US00/16064

§ 371 (c)(1),
(2), (4) Date: May 1, 2002

(87) PCT Pub. No.: WO00/76575

PCT Pub. Date: Dec. 21, 2000

Related U.S. Application Data

(60) Provisional application No. 60/207,677, filed on May 26, 2000, provisional application No. 60/140,257, filed on Jun. 18, 1999, provisional application No. 60/138,738, filed on Jun. 11, 1999.

(51) Int. Cl.[7] .............................................. A61B 5/00
(52) U.S. Cl. ...................................... 600/344; 600/309
(58) Field of Search .............................. 600/344, 322, 600/310, 309, 476, 473

(56) References Cited

U.S. PATENT DOCUMENTS

| | | | |
|---|---|---|---|
| 4,025,964 A | 5/1977 | Owens | |
| 4,112,941 A | 9/1978 | Larimore | |
| 4,274,418 A | 6/1981 | Vesterager et al. | |
| 5,556,372 A | 9/1996 | Talish et al. | |
| 5,568,806 A * | 10/1996 | Cheney, II et al. | 600/373 |
| 5,671,317 A * | 9/1997 | Weishaupt et al. | 385/137 |
| 5,879,373 A | 3/1999 | Roper et al. | |
| 5,885,211 A | 3/1999 | Eppstein et al. | |
| 6,093,156 A * | 7/2000 | Cunningham et al. | 600/573 |
| 6,381,489 B1 * | 4/2002 | Ashibe | 600/476 |

FOREIGN PATENT DOCUMENTS

| | | |
|---|---|---|
| DE | 198/24036 A | 6/1999 |
| WO | WO 98/00193 | 1/1998 |
| WO | WO 98/56293 | 12/1998 |
| WO | WO 90/04354 A | 5/1999 |

* cited by examiner

*Primary Examiner*—Eric F. Winakur
*Assistant Examiner*—Matthew J Kremer
(74) *Attorney, Agent, or Firm*—Altera Law Group, LLC

(57) ABSTRACT

An alignment device and related systems and methods for aligning at least one apparatus with respect to a surface of a tissue. The alignment device comprises a tissue interface member suitable for positioning on the surface of the tissue and mating with the apparatus to maintain alignment of the apparatus during an operation of the apparatus. The alignment device is useful to align various apparatus that are part of a continuous analyte monitoring system.

42 Claims, 17 Drawing Sheets

INTEGRATED ALIGNMENT DEVICES, SYSTEM, AND METHODS FOR EFFICIENT FLUID EXTRACTION, SUBSTANCE DELIVERY AND OTHER APPLICATIONS

This application claims the benefit of U.S. Provisional application Ser. No. 60/138,738 filed Jun. 11, 1999, entitled Methods for Operating and Features of a Continuous Glucose Monitoring System, U.S. Provisional application Ser. No. 60/140,257 filed Jun. 18, 1999, entitled System and Method for Alignment of Micropores for Efficient Fluid Extraction and Substance Delivery, and U.S. Provisional Application No. 60/207,677 filed May 26, 2000, entitled Integrated System Combining Alignment Ring and Thermal Ablating Dye that Simultaneously Removes from Alignment Ring with Optical Porator. The entirety of these above-mentioned U.S. Provisional applications is incorporated herein by reference.

BACKGROUND OF THE INVENTION

1. Field of Invention

This invention relates to an alignment system and methods for aligning at least one apparatus with respect to a surface of a tissue by utilizing a tissue interface member and mating the apparatus to the tissue interface member during the operation of the apparatus. Furthermore, this invention could have direct application in any situation where accurate, repeatable repositioning of one object with respect to another is needed, specifically for positioning an object on the surface of a tissue in a repeatable manner. For example, the coupling of any type of sensor, monitor, or device (accelerometer, thermometer, pulse pressure monitor, electrode for sensing or delivering, etc.) could benefit from a reliable method of repositioning and guaranteed alignment. This invention may be used for either application of several of the same devices for comparison, or reapplication of the same device at prescribed intervals in time so long as the original tissue interface member can remain attached to the skin unaffected.

2. Discussion of the Art

Previously, applications involving multiple or repeated engagement of an apparatus to a surface required hand-eye coordination for alignment. Often, this would lead to inaccurate alignment that would result in a less efficient and/or effective operation of the apparatus. The hand-eye coordination sometimes required a means for marking the desired location on the surface so as to use that marking as a reference point for subsequent alignment. However, this created a dependency on the operator that would lead to inconsistent results. In the field of continuous analyte monitoring of a biological tissue, oftentimes openings on the surface of the tissue are required to measure biological fluids. Techniques to create small openings in the tissue include the use of mechanical devices, thermal ablation and direct energy absorption. Where energy emitter devices are involved in the process, it is necessary to align the energy emitter device properly. For example, one thermal ablation technique creates openings utilizing a strip of energy absorbing film that is held in contact with the tissue. The film is responsive to energy directed thereon to heat up and to conductively transfer heat to the surface of the tissue to ablate the tissue. See, for example, U.S. Pat. No. 5,885,211 for a further description of this thermal ablation technique.

Furthermore, in minimally invasive continuous analyte monitoring applications, the tissue ablation process creates openings to which vacuum can be applied to extract interstitial fluid or blood for measurement, or at which point a drug delivery device may be attached at the registration/poration site to deliver the desired drug through the openings. In situations where energy emissions are used to ablate the tissue, effective fluid collection, delivery and other handling processes can be hampered by the presence of the energy absorbing film. Moving the film out of the way for collection solves the interference problem, but then site registration for placement of the fluid extraction device and substance delivery device becomes an issue. This invention provides for a tissue interface member that maintains the desired alignment after removal of the dye layer so as to enable fluid extraction and substance delivery devices to operate at the desired registration site.

There is room for improving alignment methods, systems and devices where multiple apparatus and/or repeated apparatus application to a desired location on a surface is necessary and/or beneficial for effective use of an apparatus. Particularly in the area of continuous analyte monitoring, there exists a need to integrate and consolidate several functions of the analyte monitoring procedure into a single device. The present invention and its various embodiments accomplishes and satisfies this need by providing for an efficient means to make and maintain alignment of tissue breaching devices and sensors while also removing steps otherwise necessary for interfacing and operating those apparatus at the desired location on the surface of a tissue.

SUMMARY OF THE INVENTION

The present invention is directed to an alignment device integrating a tissue interface member suitable for positioning at a desired location on the surface of the tissue and mating with an apparatus so as to maintain alignment of the apparatus during its operation. This device can be used with various types of apparatus. For example, when applied in a continuous analyte monitoring system, the apparatus may be an energy emitter device commonly used to thermally ablate the surface of the tissue. Other types of apparatus that may be used include devices such as those utilizing mechanical or heated wire techniques. In addition, alignment of devices such as a sensor that measures analyte concentration or a drug delivery device is also an important part of a monitoring system.

Systems and methods integrating the tissue interface member are also disclosed herein so that reliable and repeatable methods to properly center the desired apparatus may be applied. When applied to the field of continuous analyte monitoring, this integrated system allows for a poration mechanism to be applied and guarantees alignment as well as giving the user easy access to attach a device to the exposed adhesive site. In various embodiments of the invention, the tissue interface member adheres onto the skin and remains in its original position unaffected.

As will be evident by the following detailed description and the drawings herein, it will become apparent to one skilled in the art that the present invention and its various embodiments can be applied to numerous other systems for which alignment or repositioning at a specific centered location on a surface for continuous or numerous measurements is desired.

DETAILED DESCRIPTION OF THE INVENTION

Definitions

Figure 1A:
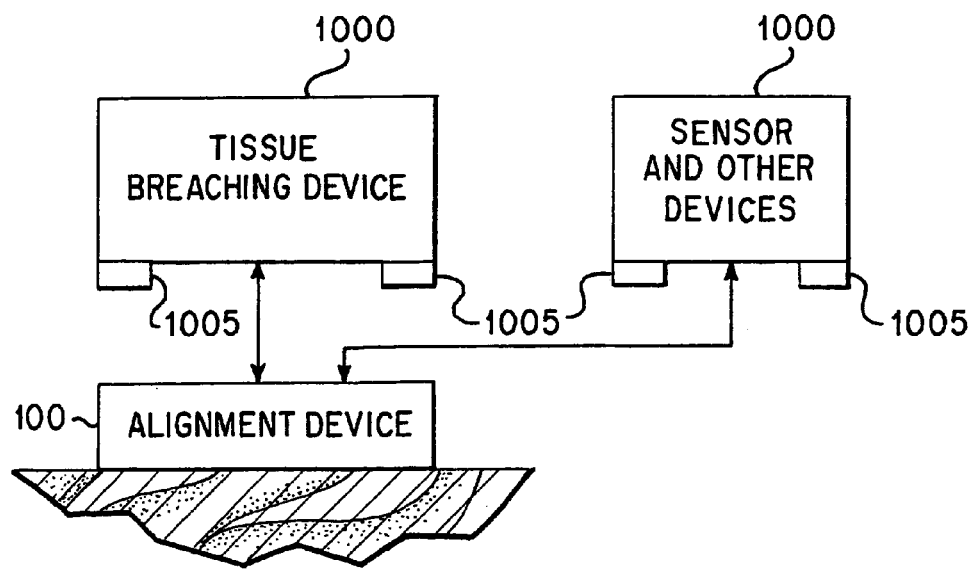
FIG. 1A is a block diagram generally showing the environment of the alignment device according to the present invention.

As used herein, the term "biological membrane" means the structure separating one area of an organism from another area of the organism, such as a capillary wall, or the outer layer of an organism which separates the organism from its external environment, such as skin, buccal mucosa or other mucous membrane. The term "epithelial tissue," when used herein is mean to mean skin, mucosa and linings of the body cavities of an organism.

As used herein, the term "tissue" means an aggregate of cells of a particular kind, together with their intercellular substance, that forms a structural material. The preferred tissue is the skin; however, other tissues suitable for use with this invention include mucosal tissue and soft organs. These examples, as are other examples used throughout this specification, are for illustrative purposes only and are not intended to be inclusive of all possibilities or suitable uses.

As used herein, the term "suction" or "pressure" relates to the relative pressure as compared to the internal pressure of the organism to which the system is interfaced. "Vacuum" is used synonymously with the term "suction."

As used herein, "ablation" refers to the process of controlled removal of a selected area of tissue from the surrounding tissue by kinetic energy released when the temperature of vaporizable substances in the selected area is rapidly elevated above the vaporization point thereby flash vaporizing some of the tissue in the selected area.

As used herein, the term "biological fluid" means blood serum, whole blood, interstitial fluid, lymph fluid, spinal fluid, plasma or any combination of these fluids. "Interstitial fluid" means the clear fluid that occupies the space between the cells in the body.

As used herein, "poration," "microporation," or any such similar term means the artificial formation of a small hole, opening or pore to a desired depth in or through a biological membrane, such as skin or mucous membrane, or the outer layer of an organism to lessen the barrier properties of this biological membrane to the passage of biological fluids, such as analytes from within the biological membrane or the passage of permeants or drugs from without the biological membrane into the body for selected purposes, or for certain medical or surgical procedures. The size of the hole or "micropore" so formed is approximately 1–1000 $\mu$m in diameter. It is to be understood that the term "micropore" is used in the singular form for simplicity, but that multiple openings or pores may be formed by the integrated device according to the present invention.

As used herein, "opening" means any physical breach of the biological membrane of a suitable size for delivering or extraction fluid therethrough, including, but not limited to, micropores.

The term "porating element" is meant to include any means of forming a micropore, hole or opening described above, including by thermal ablation, mechanically breaching the tissue by lancet or needle, and other known techniques. Several types of tissue breaching techniques, including thermal ablation methods, are disclosed in U.S. Pat. No. 5,885,211. An example of a mechanical porator device is disclosed in commonly assigned published PCT Application WO 9800193, entitled, "Multiple Mechanical Microporation Of Skin Or Mucosa." Another porating technique suitable for use in connection with this system is disclosed in commonly assigned PCT Application No. PCT/US99/15967 entitled "Controlled Removal Of Biological Membrane By Pyrotechnic Charge For Transmembrane Transport," filed Jul. 14, 1999.

The term "heated probe" or "heat conducting element" means a probe, preferably solid phase, which is capable of being heated in response to the application of electrical, mechanical, sonic, magnetic, electromagnetic or optical energy thereto for achieving thermal ablation of the tissue. For simplicity, the probe is referred to as a "heated probe" or "heatable probe" which includes a probe in a heated or unheated state, but which is heatable.

The term "continuously" when used in connection with a continuous analyte monitoring system, means acting on an ongoing basis at a frequency or event rate that may vary depending on a particular application of the system. For example, the output of the sensor may be read on a periodic basis, such as every minute, several minutes, hour, several hours, etc. Moreover, at each reading event the sensor output is optionally sampled multiple times so as to obtain a plurality of readings relatively close in time whereby an average or other adjustment of those multiple readings is made for determining a final reading that is displayed or logged. An example of a continuous monitoring system is disclosed in PCT Application No. PCT/US99/16378, filed Jul. 20, 1999, and entitled System and Method for Continuous Analyte Monitoring.

The term "apparatus" means tissue breaching devices, such as an energy emitter device (laser), micro-lancets, micro-needles, and other mechanical tissue breaching devices, an electrically heated element device for performing thermal ablation as disclosed in U.S. Pat. No. 5,885,211, a sensor device such as an analyte sensor (glucose, etc.), and a drug delivery device, or any other type of device used to interface with a surface of the biological tissue for the desired operation of the device.

The present invention is directed to an alignment device suitable for positioning on the surface of the tissue, preferably at a desired location on the surface of the tissue, and to systems and methods for using the alignment device. Referring to FIG. 1A, the alignment device, shown generally at 100, is positioned, attached or placed on the surface of a tissue, such as skin. The alignment device 100 mates with apparatus 1000 that may be one of a variety of tissue breaching devices, sensors, etc. The apparatus 1000 include at least one alignment member 1005 that mates or engages with complementary alignment members of the alignment device 100.

Figure 1B:
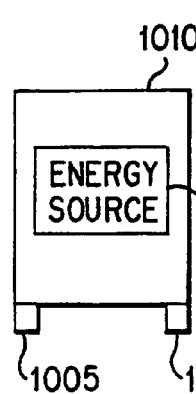
FIG. 1B is a block of an energy emitter apparatus having alignment features according to the present invention.

FIGS. 1B through 1E illustrate examples of the various types of apparatus 1000 that mate with the alignment device 100, all of which may include any one or more of the specific alignment structures disclosed hereinafter. FIG. 1B illustrates an energy emitter device 1010 comprising at least one energy source 1015, such as a laser. An example of a suitable laser device is disclosed in U.S. Pat. No. 5,885,211. The energy source 1015 may be a type that is used together with an energy absorbing material, such as an optical energy absorbing dye film, to ablate tissue by thermal ablation. Alternatively, the energy source 1015 may be a type that is used to cause the direct absorption of energy to ablate the tissue. In either case, alignment to the tissue surface is achieved by providing at least one alignment member 1005 on the energy emitter apparatus that mates with the alignment device 100.

Figure 1C:
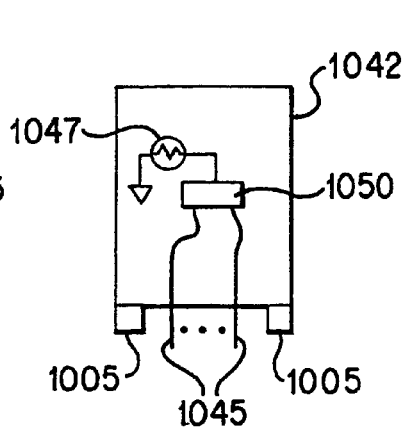
FIG. 1C is a block diagram of an electrically heated element tissue breaching device having alignment features according to the present invention.

FIG. 1C shows a heated element tissue breaching device 1042 comprising one or more electrically heatable elements 1045. Electrical current is supplied to the heatable elements 1045 from a current source 1047 under control of a controller 1050. Further details of the device 1042 are disclosed in U.S. Pat. No. 5,885,211 and in PCT Application No. PCT/US99/04990, filed Mar. 5, 1999. The device 1042 includes at least one alignment member 1005 to mate with the alignment device 100 and thereby properly aligns the elements 1045 with the tissue surface via the alignment device 100.

Figure 1D:
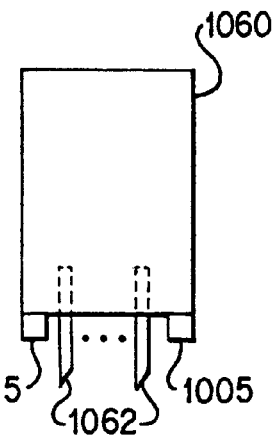
FIG. 1D is a block diagram of a mechanical tissue breaching device having alignment features according to the present invention.

FIG. 1D illustrates a mechanical tissue breaching device 1060 comprising at least one tissue piercing element 1062, such as a micro-lancet or micro-needle. The device 1060 has at least one alignment member 1005 to mate with the alignment device 100 and properly align the tissue piercing element 1062 with the tissue surface. The tissue piercing element 1062 may be retracted in the device 1060 when not in use, and released into the tissue by one of a variety of mechanisms known in the art, such as those used in glucose test kits. Alternatively, the device 1060 may comprise a plurality of tissue penetrating members fabricated using micro-lithographic techniques as described in aforementioned PCT Application No. WO 9800193.

Figure 1E:
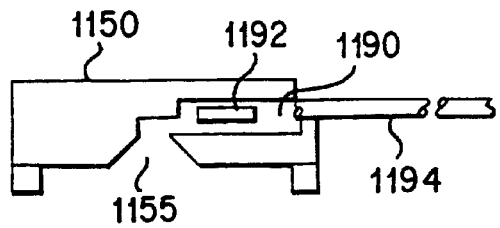
FIG. 1E is a diagram of a fluid collection and sensor device having alignment features according to the present invention.

FIG. 1E illustrates basic components of a fluid collection and sensor device 1150. The device 1150 has at least one alignment member 1005 to mate with the alignment device 100 in order to position a harvesting head or opening 1155 with openings made in the tissue beneath the alignment device. The fluid collection and sensor device 1150 further comprises an assay element 1192 positioned in or proximate a fluid collection chamber 1190. The assay element 1192 is responsive to one or more substances in the fluid collected from the tissue, such as glucose. Fluid from the tissue is drawn into contact with the assay element 1192 under application of vacuum supplied via a cable 1194. The details of a suitable fluid collection and sensor device are disclosed in PCT Application Nos. PCT/US00/09393, filed Apr. 7, 2000, PCT/US99/16226, filed Jul. 20, 1999, and PCT/US99/16378, filed Jul. 20, 1999, the entirety of which is incorporated herein by reference.

Examples of other apparatus include monitors, thermometers, pulse pressure monitors, accelerometers, sensing or stimulating electrodes, etc. Regardless of the type of apparatus used, the present invention provides a means for repeatable, reliable and guaranteed alignment at the desired position to which the alignment device may be attached.

In various embodiments, the present invention is described as being useful in continuous analyte monitoring. In such instances, the present invention allows for a reliable and repeatable method to properly center a fluid harvesting device (also called a fluid collection and sensor device). This integrated system allows for a tissue breaching device to be applied and guarantees alignment as well as giving easy access to attach a device to the exposed site. The tissue interface member can adhere to the tissue and remain in its original position unaffected. Although various embodiments of the present invention are directed towards continuous analyte monitoring, it will become apparent to one skilled in the art that the present invention could be used with various applications to other uses that require alignment with a specific centered location on the surface of a tissue for continuous or numerous measurements, applying therapies of any variety, and creating openings in the tissue of any size, etc.

Figure 2A:
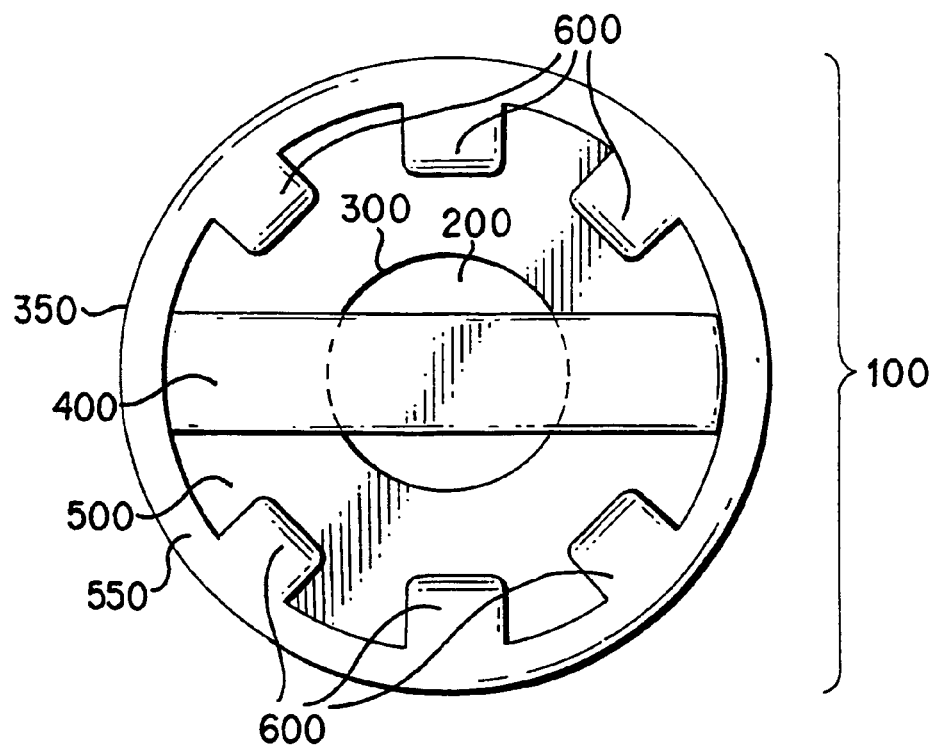
FIG. 2A is a top view of a tissue interface member having biased clips according to one embodiment of the invention.
Figure 2B:
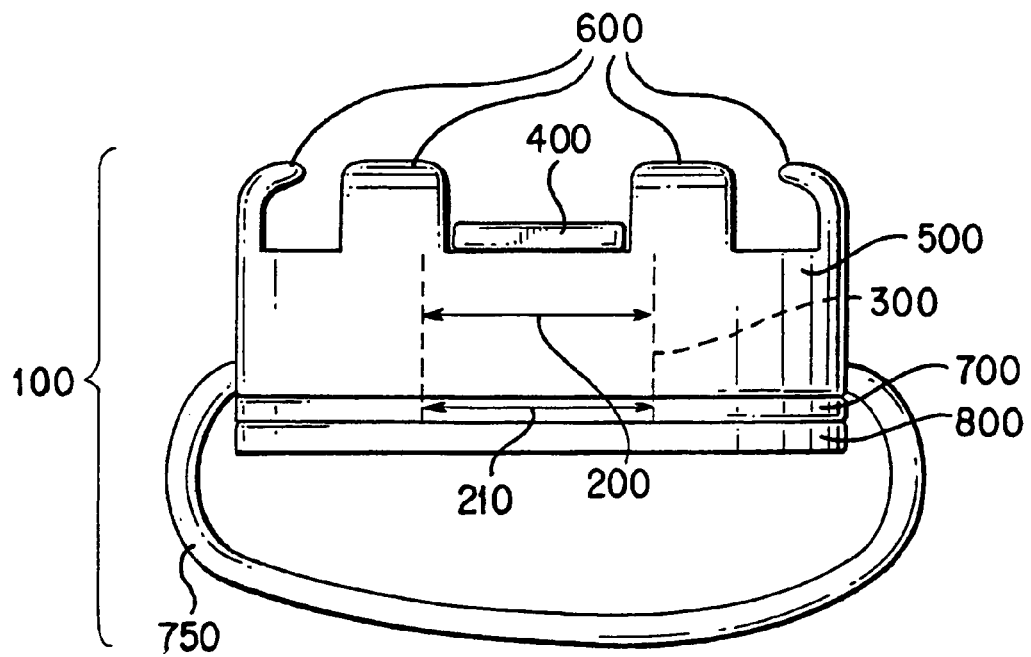
FIG. 2B is a side view of the tissue interface member shown in FIG. 2A.
Figure 2C:
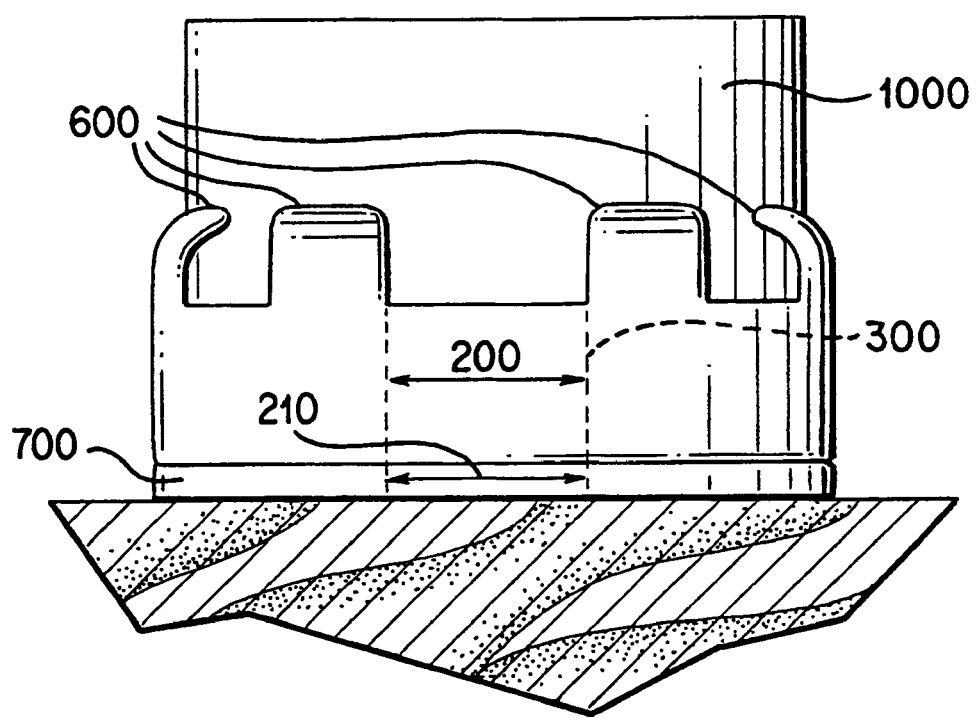
FIG. 2C is a view of the tissue interface member of the embodiment of the invention, as shown in FIGS. 2A and 2B, attached to an apparatus.

According to one embodiment of the present invention, FIGS. 2A and 2B show the alignment device 100 comprising a tissue interface member 500 having a raised perimeter 550 along the circumference thereof with at least one clip 600 extending therefrom. The clip 600 is biased by virtue of its inwardly curved lip or other structural feature (known in the art of mechanical clip design) so that it engages an apparatus inserted therein and holds it in engagement with the tissue interface member 500. Furthermore, the tissue interface member 500 has an opening or passageway 200 circumscribed by an interior surface 300 of the tissue interface member 500. With reference to FIG. 2C, when an apparatus 1000 is properly inserted into the tissue interface member 500 and snapped into place beneath the clip(s) 600, the tissue interface member 500 holds the apparatus 100 in a predetermined or desired relationship with respect to the opening 200, and thus with a tissue surface underlying the opening as shown in FIG. 2C. This allows the apparatus 1000 to interact with the surface of the tissue at the desired location maintained by the alignment device 100. FIGS. 2A–2C are enlarged and are not to scale (particularly as to the thickness of the device) in order to illustrate the various structural features of the alignment device.

When the tissue breaching device involves an energy emitter apparatus, oftentimes energy absorbing film is used therewith. The film is responsive to energy directed thereon to heat up and to conductively transfer heat to the surface of the tissue to ablate the tissue. Such an optical thermal ablation process is disclosed in aforementioned U.S. Pat. No. 5,885,211. Referring back to FIG. 2A in conjunction with FIG. 2B, an energy absorbent layer 400 is shown placed across the top of the opening 200 of the tissue interface member 500. An adhesive layer 700 and a release liner 800 are provided on a bottom surface of the tissue interface member 500 for attaching the alignment device 100 to the surface of a tissue. When the alignment device 100 is attached via the adhesive layer 700, the release liner 800 is first removed so that the adhesive layer 700 may be exposed and attached to the desired location on a surface. The adhesive layer 700 also has an opening or passageway 210 therein circumscribed by the interior 305 of the adhesive layer 710. Moreover, the adhesive layer opening 210 is in alignment with the opening 200 of the tissue interface member 500. In the alternative or in combination, the alignment device 100 can further comprise a strap 750 that attaches to the tissue interface member 500 and extends around a body portion of an user, such as an arm, leg, or waist, so as to mount and hold the tissue interface member 500 at the desired location on the surface of the tissue for the desired duration of time.

Figure 3:
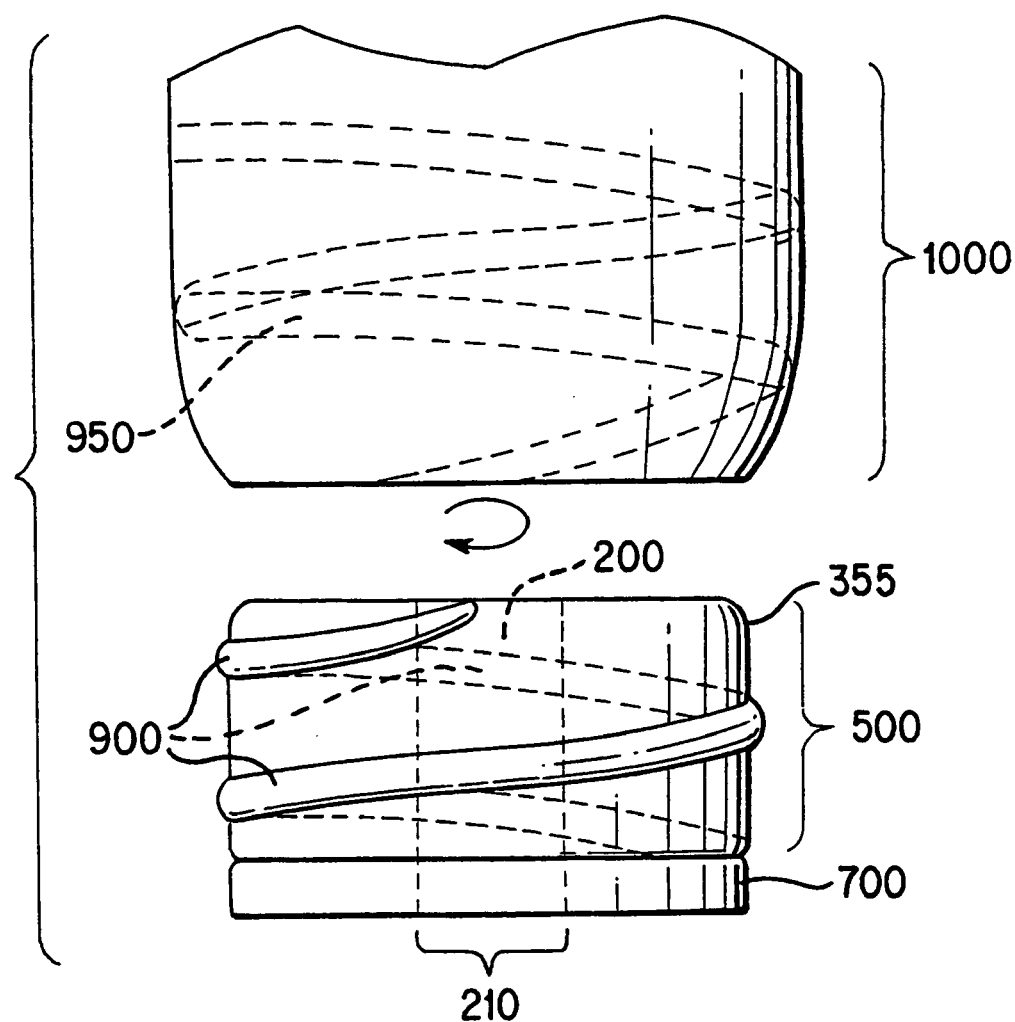
FIG. 3 illustrates the tissue interface member according to another embodiment of the invention, mating with an apparatus having a complementary threaded surface.

According to another embodiment shown in FIG. 3, the tissue interface member 500 may engage with an apparatus via a threaded member 900 that circumscribes a side exterior surface 355. Like FIGS. 2A–2C, FIG. 3 is not drawn to scale in order to best illustrate the invention. The opening 200 longitudinally traverses through the tissue interface member 500 and is aligned with the adhesive layer opening 210 of the optional adhesive layer 700. FIG. 2 illustrates how a surface of an apparatus 1000 has a complementary threaded member 950 therein that mates with the threaded member 900 of the tissue interface member 500.

FIGS. 4A–4E are directed to another embodiment of an integrated alignment device according to the present invention. In this embodiment, the integrated alignment device 100 is designed for an application that involves the use of an energy emitter device and an energy absorbent layer 400, in cooperative operation, to ablate the surface of a tissue. The alignment device 100 comprises a tissue interface member 500 that is circular in shape with an opening 200 therein and several layers attached thereto to facilitate placement on the surface of the tissue and engagement of various apparatus.

Figure 4A:
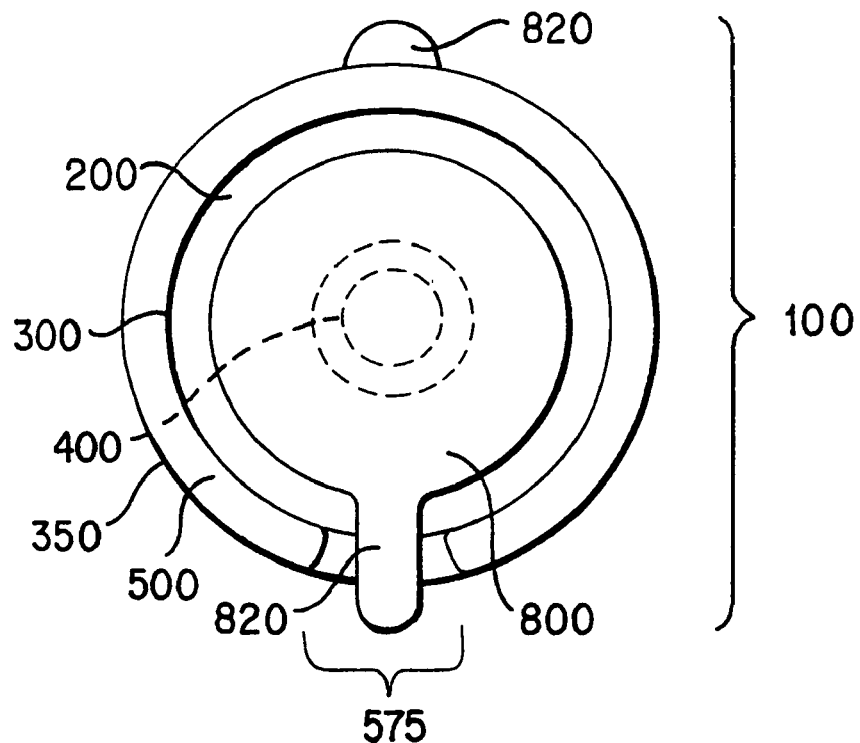
FIG. 4A is a top view of tissue interface member and energy absorbing layer according to another embodiment of the present invention.
Figure 4B:
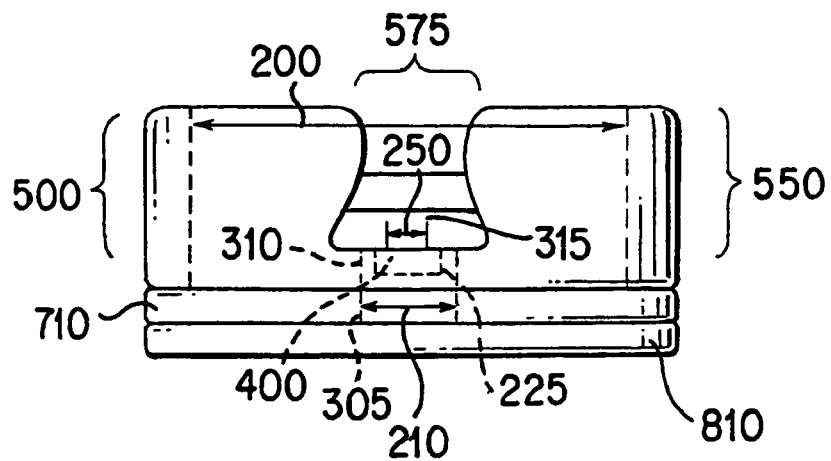
FIGS. 4B and 4C show the side view of elements of the embodiment of the invention shown in FIG. 4A.

As shown in FIG. 4B, several release liner/adhesive layers are in a sandwich-type configuration. There is a bottom double-sided adhesive layer 710 attached on its top side to the bottom of the tissue interface member 500 and covered on its bottom side by a bottom release liner 810. This bottom release liner 810 may be removed so that the bottom adhesive layer 710 and the tissue interface member 500 may adhere to the skin. The bottom adhesive layer 710 preferably is one that is not irritable, toxic or otherwise hazardous to the skin but is strong in its adhesiveness to allow the tissue interface member 500 to remain attached to the surface of the skin when used with multiple applications of an apparatus to the tissue interface member 500. An example of such type of an adhesive commonly used is the Brandon 2656B double adhesive. The bottom adhesive layer 710 also has an opening 210 therein that is circumscribed by the interior surface 305 of the bottom adhesive layer 710. This adhesive opening 210 is smaller in diameter than the diameter of the tissue interface member 500. The tissue interface member 500 is attached along the perimeter of the top side of the bottom adhesive layer 710. Above the bottom adhesive layer 710 and within the tissue interface member 500, there is a carrier layer (not shown) with an aperture 225 that contains an energy absorbent layer 400 therein aligned with the adhesive opening 210. A pocket or gap 575 is provided to allow room for a cable that may connect to an apparatus that mates with the tissue interface member shown in these diagrams. The internal elements of the tissue interface member 500 are better shown in FIG. 4C.

Figure 4C:
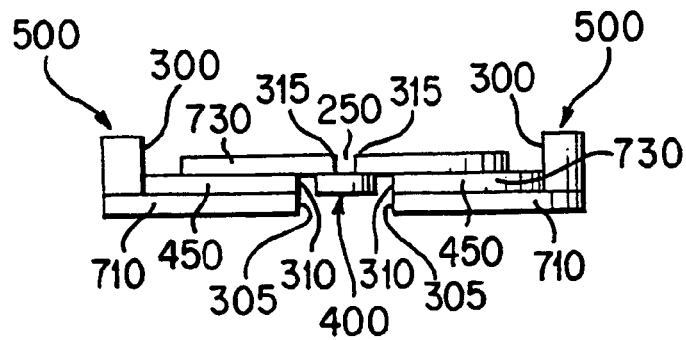

Turning to FIG. 4C, the area of the top side of the bottom adhesive layer 710 circumscribed by the interior surface 300 of the tissue interface member 500 is attached to the non-sticky (e.g. silicon) surface of a carrier layer 450. An example of a carrier layer that may be used is the Kraft Release Liner with a silicon surface on one side and a paper surface on the other side. The carrier layer 450 also has a carrier layer aperture 225 therein circumscribed by the interior surface 310 of the carrier layer 450. The carrier layer aperture 225 is in alignment with the adhesive opening 210 and may be the same size or smaller. Within the carrier layer aperture 225 lies an energy absorbent layer 400 that is concentric to but smaller than the carrier layer aperture 225 and in alignment with the carrier layer aperture 225 and the adhesive opening 210. The energy absorbent layer 400 is fixed in its position within the carrier layer aperture 225 by the bottom side of a top double adhesive layer 730. The top double-sided adhesive layer 730 also fits within the opening 200 circumscribed by the interior surface 300 of the tissue interface member 500. Furthermore, the top double-sided adhesive layer 730 has an orifice 250 therein that is also circumscribed by the interior surface 315 of the top double-sided adhesive layer 730. The orifice 250 is concentric to but smaller than the carrier layer aperture 225 and again is in alignment with the carrier layer aperture 225 and the adhesive opening 210. The size and alignment of the orifice 250 allows the top double-sided adhesive layer 730 to circumscribe and overlap the interior perimeter of the carrier layer aperture 225. This overlap provides the surface area to which the energy absorbent dye layer 400 may attach enabling it to be fixed in such a position so that it suspends with the carrier layer aperture 225. Finally, a non-sticky side of the top release liner 830 attaches to the top of the top double-sided adhesive layer 730 until the alignment device 100 is ready to be used. Similar to the bottom release liner 810, the top release liner 830, as shown in FIG. 4A, also has an extended flap portion 820 for the user to grab to facilitate the removal of the release liner.

Figure 4D:
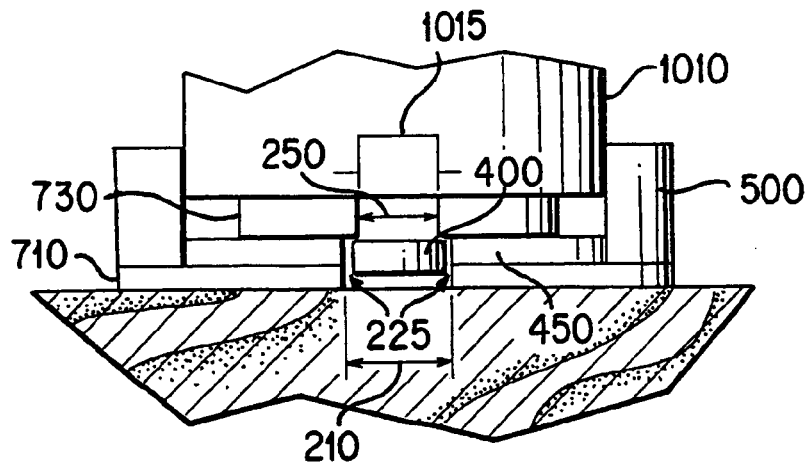
FIGS. 4D and 4E illustrate the embodiment of the inventions as shown in FIGS. 4A–4C, inclusively, as used in a continuous analyte monitoring system.
Figure 4E:
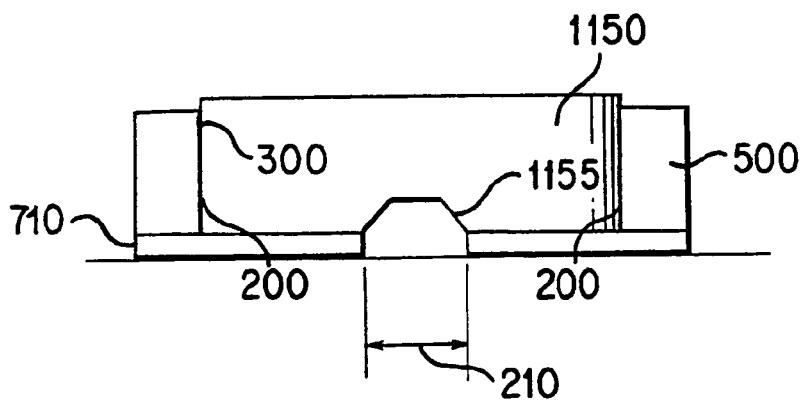

FIGS. 4D and 4E show how the alignment device of FIGS. 4A–4C is used in a continual analyte monitoring system. Once the bottom release liner 810 is removed, the tissue interface member is attached to the surface of the tissue (skin) via the bottom adhesive layer 710. The top release liner 830 is then removed and an energy emitter device 1010 (such as a laser diode apparatus) is inserted into the tissue interface member 500 and engages the top double-side adhesive layer 730. The tissue interface member 500 is already attached to the surface of the tissue via the bottom adhesive layer 710. When in position in the tissue interface member 500, the energy emitter device 1010 is aligned such that at least one source of an energy emission 1015 emitted by the energy emitter device 1015 is in alignment with the orifice 250 which is in alignment with the energy absorbent layer 400, which is in alignment with the carrier layer aperture 225, which in turn is in alignment with the adhesive opening 210 as shown in FIG. 4D. After the energy emission is complete, the energy emitter device 1010 can then be removed from the tissue interface member 500 leaving the integrated alignment device 100 fixed at the original alignment registration site. According to this embodiment of the invention, removal of the energy emitter device 1010 also simultaneously removes top adhesive layer 730, the energy absorbent layer 400 and the carrier layer 450 in one step, leaving the tissue interface member 500 attached to the surface of the skin by the bottom adhesive layer 710. Referring to FIG. 4E, the harvesting head 1155 of the fluid collection and sensor device 1150 may be inserted into and mated with the tissue interface member 500 which aligns the harvesting head 1155 with affected site of the tissue so that the source of suction is directly over the adhesive opening 210 and over the affected tissue site (not shown) created by the previous application of the energy emitter device.

The selection of materials and dimensions of an alignment device according to the present invention may vary with the particular application. In the case where the energy absorbing layer 400 is used in connection with a laser diode type energy emitter device, the energy absorbing layer is formed of a layer of PET (1 mil) and of Acetylene Black (2 mil) and approximately 4.9 mm in diameter. The thickness of the top adhesive layer 730 is 6.3 mil and the thickness of the bottom adhesive layer 710 is 6.0 mil. The diameter of the orifice 250 is 3.5 mm and the diameter of the opening 210 is 5.0 mm.

Figure 5:
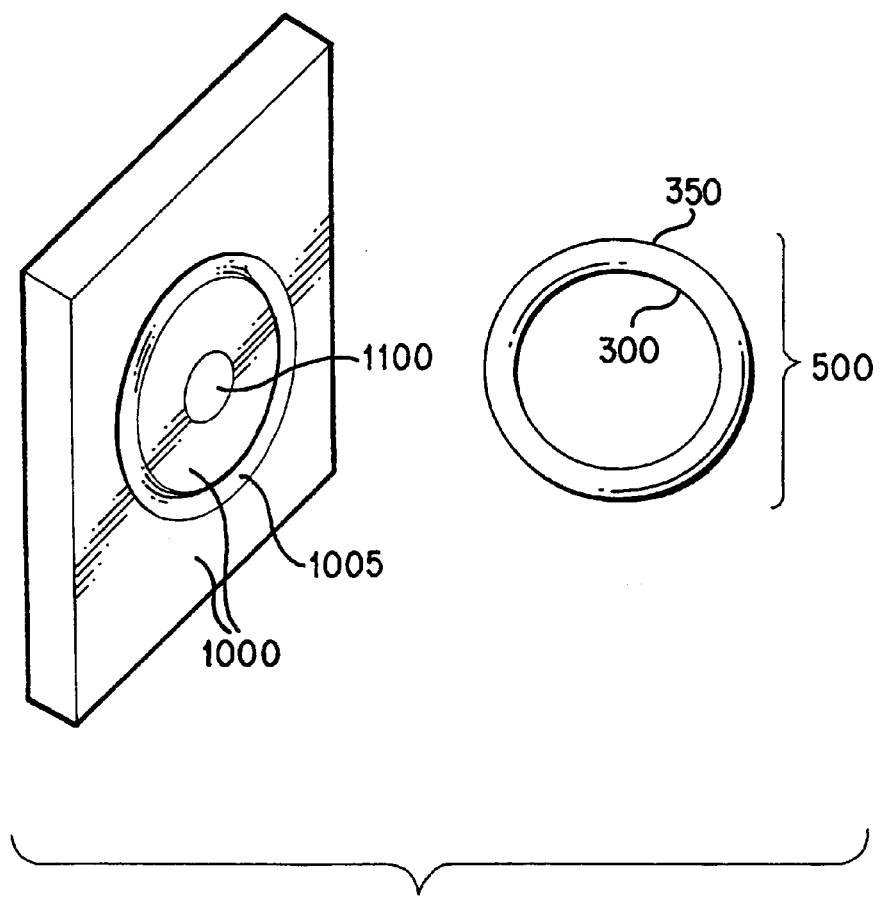
FIG. 5 is a perspective view of a tissue interface member and a portion of an apparatus that mates thereto, according to another embodiment of the invention.

Other embodiments of the invention provide for various other means for which the tissue interface member might engage with an apparatus. For example, the tissue interface member can comprise any planar geometric shape, such as a triangle, a circle, ellipse, rectangle, etc., to facilitate interface with an apparatus that contains complementary elements to mate with the tissue interface member. FIG. 5 shows an embodiment where the tissue interface member 500 comprises a circular shape with an opening 200 therein circumscribed by its interior surface 300. According to this embodiment, the interior surface 300 and the exterior surface 350 of the tissue interface member 500 mate to a complementary shaped groove or indented region 1005 of a tissue interface member engaging portion of the apparatus 1000.

Figure 6:
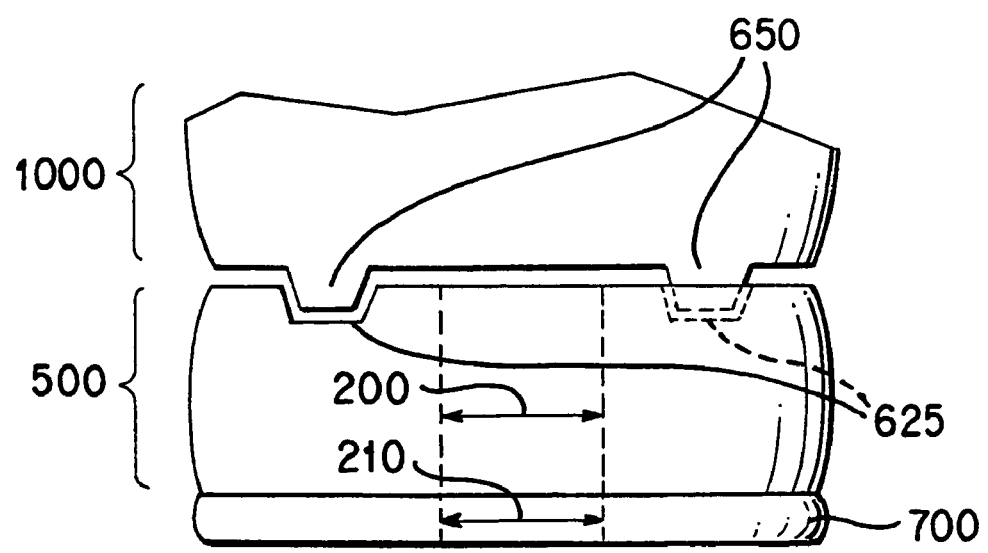
FIG. 6 is a side view of the tissue interface member according to another embodiment of the invention and mating with another apparatus.

In addition or in the alternative to any of the embodiments described herein, the tissue interface member can have additional structural features that facilitate mating with an apparatus. Examples of such characteristics include, but are not limited to, complementary magnetic surface portions, adhesive on engaging surfaces, and/or complementary male or female members. For example, FIG. 6 shows a tissue interface member that has at least one female member 625. According to this embodiment, the tissue interface member engaging portion of an apparatus 1000 has complementary male member(s) 650 that mate with the female members 625 of the tissue interface member 500 to achieve and maintain the desired alignment while the tissue interface member 500 is attached to the tissue surface. Furthermore, these male or female members can also have complementary magnetic surfaces or adhesive to enhance attachment and maintenance of the alignment between the tissue interface member 500 and the tissue interface member engaging portion of the apparatus 1000.

Figure 7A:
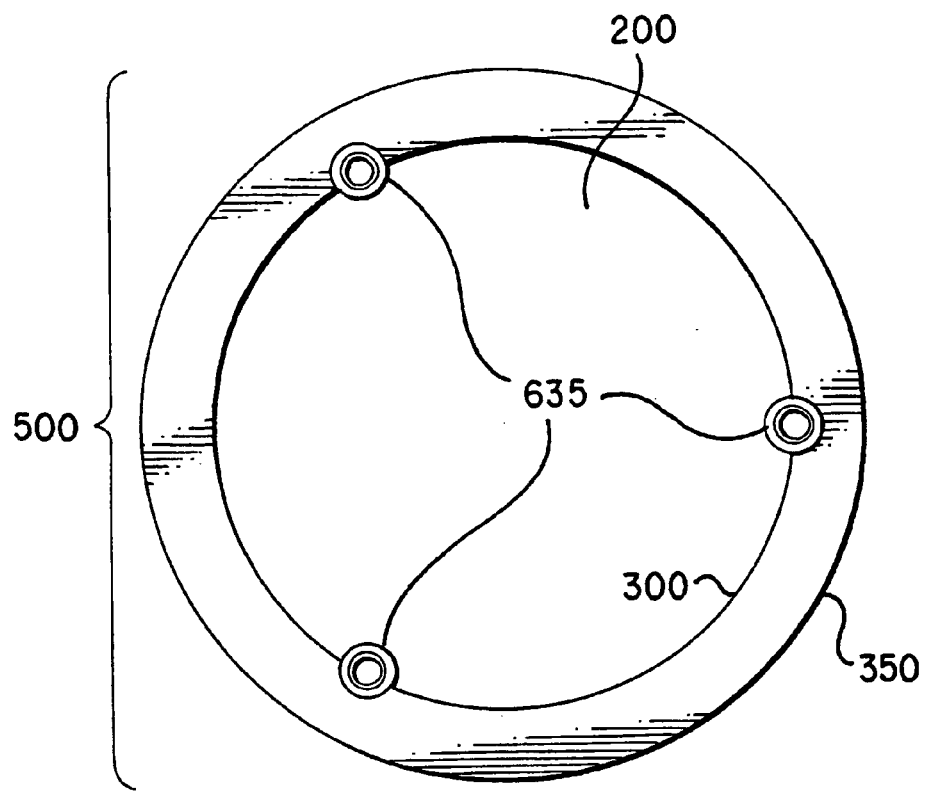
FIG. 7A is a top view of tissue interface member according to still another embodiment of the invention.
Figure 7B:
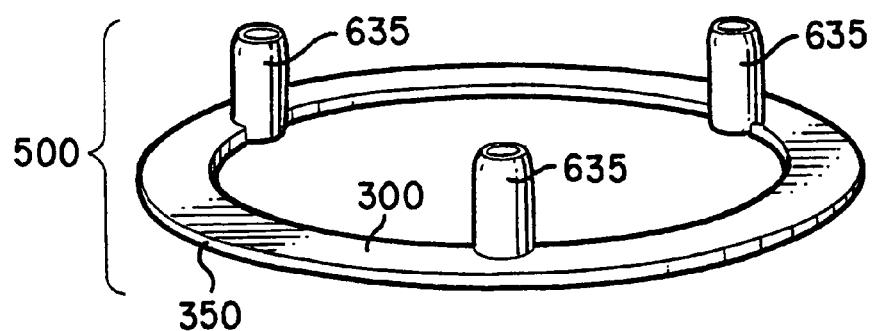
FIG. 7B is a side view of the tissue interface member shown in FIG. 7A.

FIGS. 7A and 7B illustrate another embodiment of the invention where the top surface of the tissue interface member 500 comprises of at least one male member 635 and also has an opening 200 circumscribed by the interior surface 300 so that an apparatus may interact with the surface of the tissue via opening 200. Complementary female members would be on the apparatus that are designed to mate with the tissue interface member shown in FIGS. 7A and 7B.

Figure 8A:
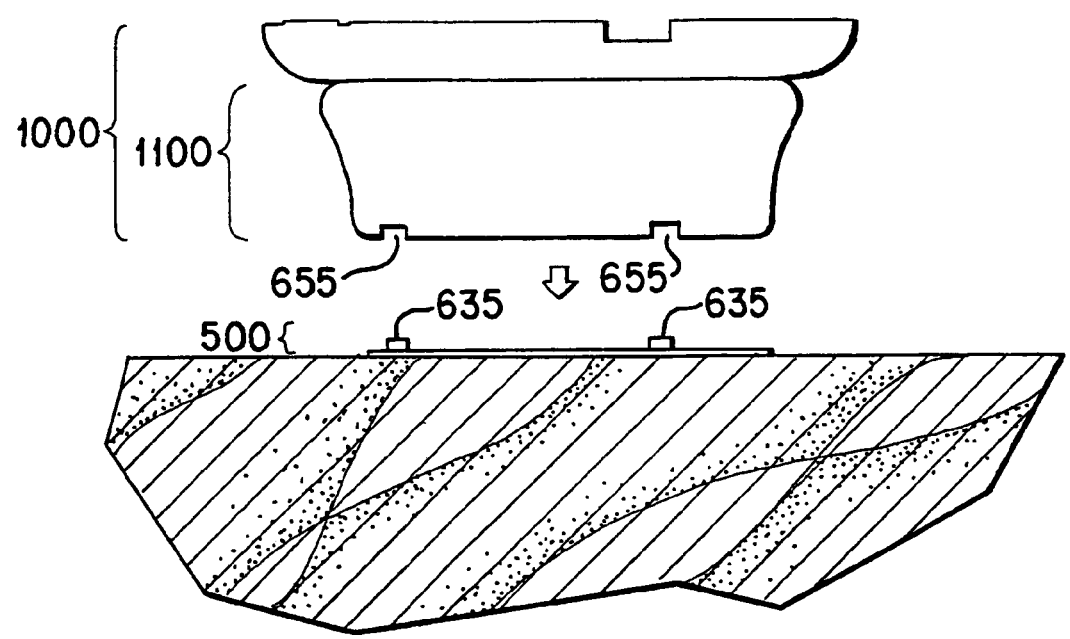
FIGS. 8A through 8G are side views showing operation steps of a tissue interface member used as part of a continuous analyte monitoring system.
Figure 8B:
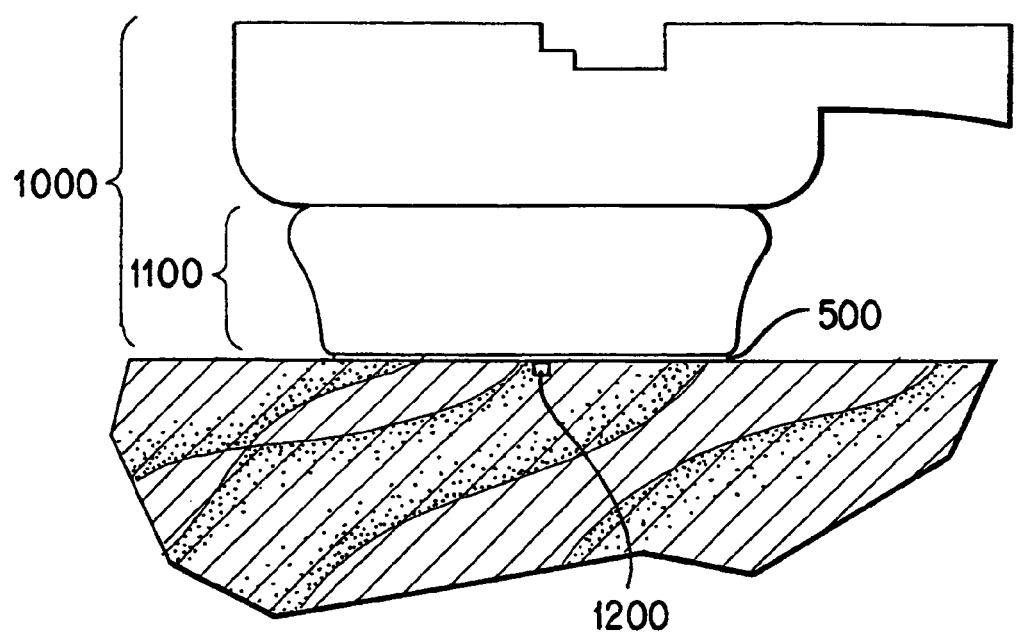
Figure 8C:
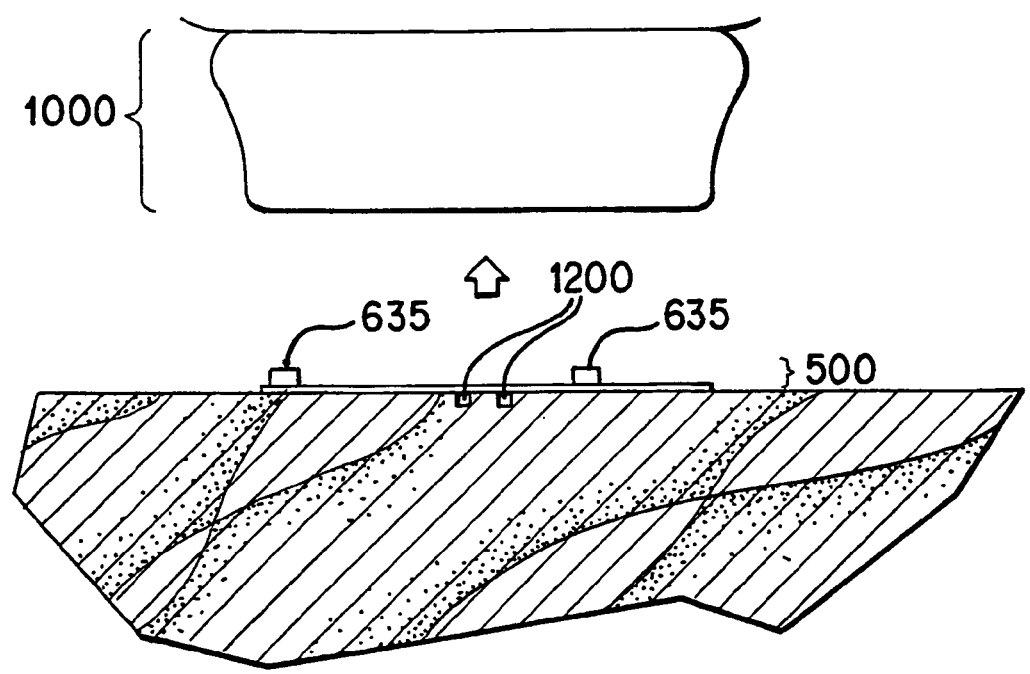
Figure 8D:
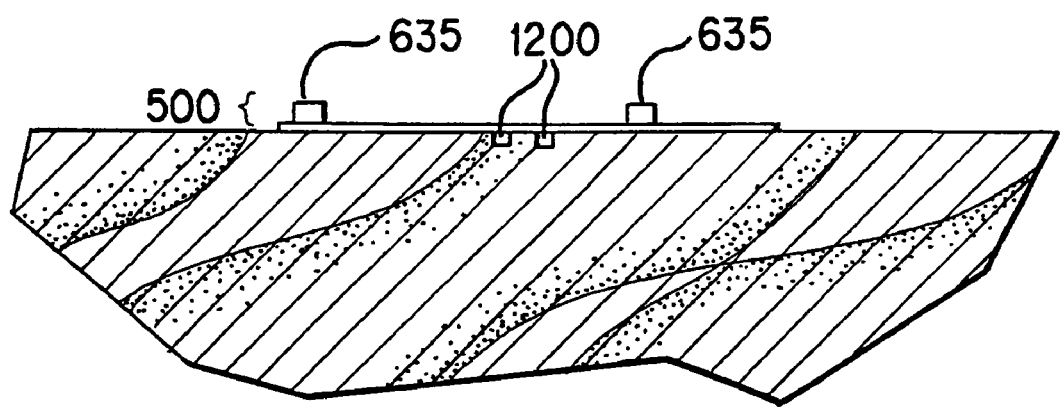
Figure 8E:
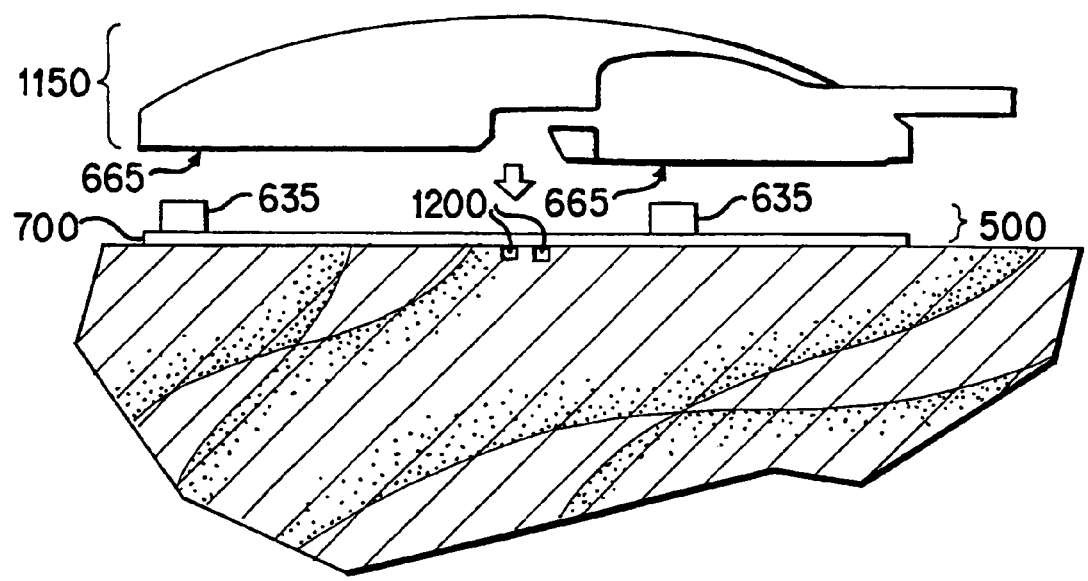
Figure 8F:
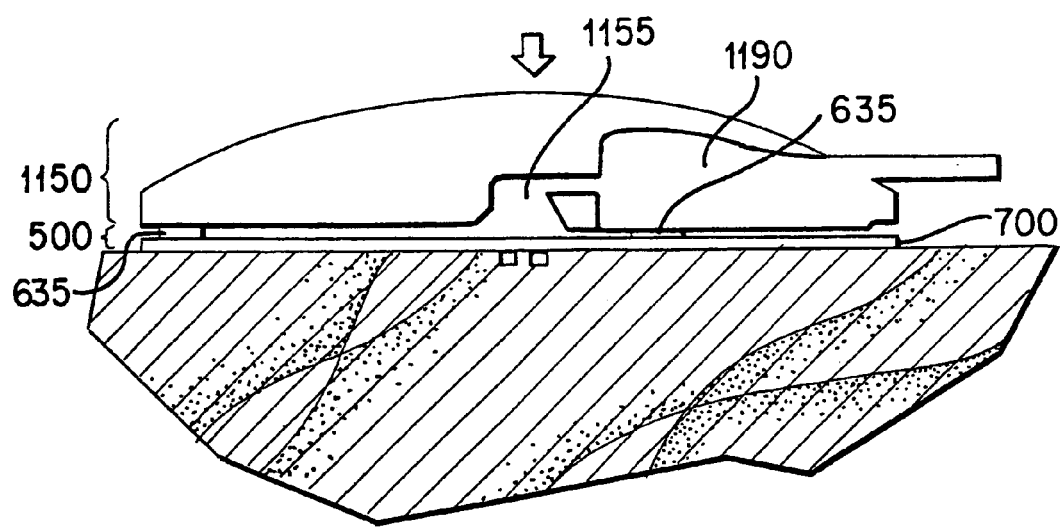
Figure 8G:
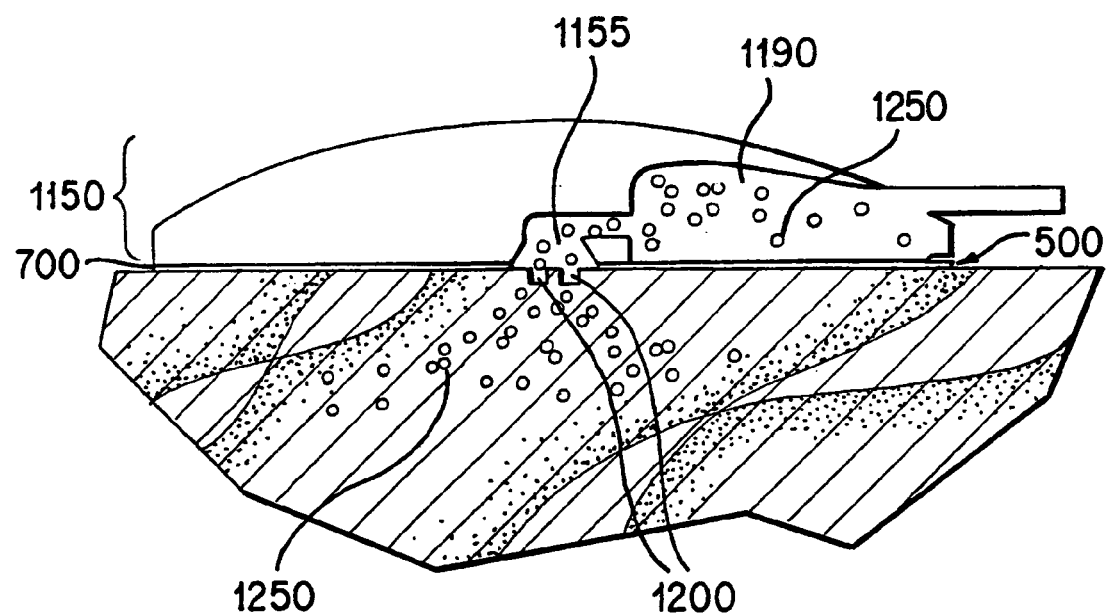

FIGS. 8A–8G inclusively show operation of an alignment device according to one embodiment of the invention (FIGS. 7A and 7B) in the context of a continual analyte monitoring system. It should be understood that the alignment device according to the other embodiments operates in a similar fashion according to its structural features. FIG. 8A shows the tissue interface member 500 attached to the surface of a skin via an adhesive (not shown). The tissue interface member 500 has at least one male member 635 as shown in FIGS. 7A and 7B. A tissue interface member engaging portion 1100 of an apparatus 1000 (in this case a tissue breaching device) with at least one complementary female member 655 is placed above the tissue interface member 500. FIG. 8B shows the tissue breaching apparatus 1100 mating with the tissue interface member 500 via their complementary male and female members, respectively. FIG. 8B also shows that the tissue breaching device 1100 has formed at least one opening 1200 through the surface of the tissue. The manner in which these openings are formed depends on the type of tissue breaching apparatus selected (mechanically piercing the tissue, thermally ablating the tissue with an electrically heated wire, thermally ablating the tissue by heating an energy absorbing layer in contact with the tissue with a beam or field of energy, emitting a beam or field of energy that is directly absorbed by the tissue to form the openings, etc.) An example of an energy emitter apparatus is an laser beam device disclosed in U.S. Provisional Applications No. 60/140,003, filed Jun. 18, 1999 and 60/165,814, filed Nov. 16, 1999, the entirety of which is incorporated herein by reference. FIG. 8C shows the tissue interface engaging portion 1100 of the tissue breaching device (not shown) detaching from the tissue interface member 500 after creating at least one opening 1200 on the surface of the tissue. The tissue interface member 500 remains attached to the surface of the tissue at the initial registration site. FIG. 8D is another view of the tissue interface member 500 remaining fixed at the original placement site after the surface of the tissue had been breached by a tissue breaching device. FIG. 8E shows the fluid collection and sensor device 1150 having complementary female members (their general location being shown by arrows 665 but not in view in FIG. 8E) that mate to male members 635 on the tissue interface member 500. The male members 635 on the tissue interface member are in a fixed and known position such that the openings 1200 formed in the tissue by the tissue breaching device are at a fixed position with respect to the tissue interface member 500. Consequently, the subsequent attachment of the fluid collection and sensor device 1150 to the tissue interface member (with female members 665 placed at a fixed and known position with respect to internal structures thereof) will achieve proper alignment with the openings 1200 to draw fluid (by vacuum) from the openings into the harvesting head 1155 (which is essentially an opening into a housing of the sensor device 1150) where the fluid collection/analysis chamber 1190 is located inside the sensor device 1150. This interaction is facilitated and enhanced by the consistent registration to the site by the tissue interface member 500. FIG. 8F shows the fluid collection and sensor device 1150 matingly engaging the tissue interface member 500 and FIG. 8G shows the fluid collection and sensor device 1150 completely engaged with the tissue interface member 1150 such that fluid 1250 in the tissue can pass through the openings 1200 in the tissue and into the fluid collection chamber 1190. A fluid collection and sensor device of this type comprises an assay element that reacts with one or more analytes, such as glucose, to provide a reading of a concentration of such one or more analytes for an individual.

Once the alignment device of the present invention is properly placed, the systems and methods of the present invention allow for new fluid collection and sensor devices to attach to the tissue interface member after poration has occurred to thereby use the same set of tissue openings formed at the location of the tissue interface member. The advantage is that the same set of openings can be used repeatedly for fluid extraction without having to make new openings. Consequently, whereas the fluid collection and sensor device may have a limited useful lifetime, new ones can be installed to use the same set of openings repeatedly for fluid extraction without having to make new openings. Similarly, for delivery applications, the same set of openings can be used for different and multiple delivery events.

According to another aspect of the present invention, a mechanism is provided to provide certain safety features and to assist in aligning an apparatus in the alignment device. These safety features may be useful to prevent tissue breaching, fluid extraction and/or substance delivery if the attachment of the apparatus device is not proper.

Figure 9:
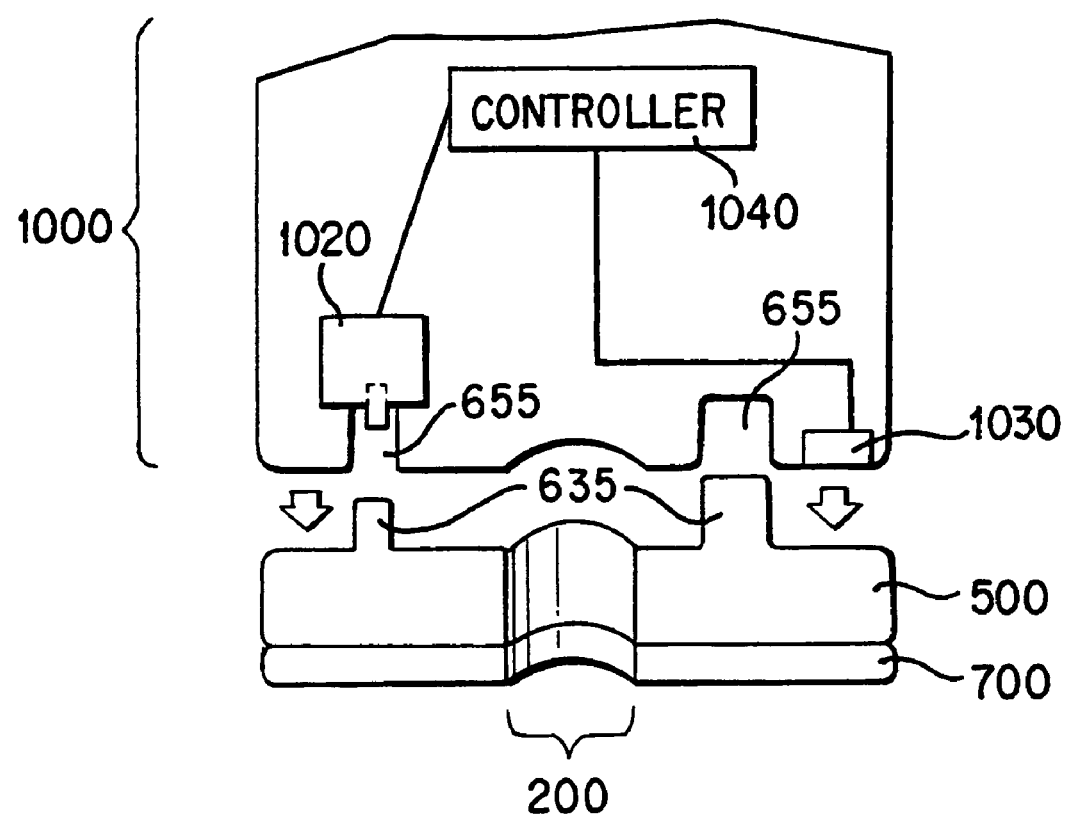
FIG. 9 is a diagram of a tissue interface member and an energy emitter device and illustrating a control activation feature according an embodiment of the present invention.

FIG. 9 shows the tissue interface member engaging portion of the apparatus 1000 having at least one female member 655 allowing it to matingly engage with at least one complementary male engaging member 635 on the tissue interface member 500. The apparatus is, for example, a laser beam device of the type referred to in the above-mentioned provisional application. However, this feature may be useful in a type of apparatus that is to be operated only when properly in position in an alignment device. A sensor 1020 is provided in the apparatus 1000 that is positioned in proximity to a female member such that it is mechanically or electrically tripped when engaged by the at least one male member 635 on the tissue interface member 500. The sensor 1020 is also electrically coupled to a controller 1040. The sensor 1020 is, for example, a switch that is closed when engaged by the male member 635 on the tissue interface member 650 when the apparatus 1000 is properly engaged in the tissue interface member 500. When the switch 1020 is closed, an enable signal is coupled to the controller 1040 (or a circuit is completed and detected by the controller 1040) which will in response, enable operation of the apparatus. While the apparatus 1000 is properly mated to the tissue interface member 500, the apparatus is fully enabled and may be activated by a control button (or other user control or automatic control mechanism) to interact with the surface of the tissue. In the embodiment shown in FIG. 9, the apparatus 1000 interacts with the surface of the tissue through the opening 200 of the tissue interface member 500. As an additional optional feature, a pressure (force) sensor 1030 is also provided that is responsive to upward pressure from the tissue interface member 500 when the apparatus 1000, such a laser beam device, is pressed downward. Sufficient downward pressure of the apparatus 1000 against the tissue interface member may be a prerequisite to enabling activation or actual activation of the apparatus. In this way, the apparatus will not be activated unless the switch 1020 detects proper engagement in the tissue interface member 500 and the pressure sensor 1030 detects that sufficient downward force is being applied to the apparatus 1000.

According to one aspect, the present invention is directed to an alignment device for aligning at least one apparatus with respect to a surface of a tissue, comprising a tissue interface member suitable for positioning on the surface of the tissue and mating with the apparatus to maintain alignment of the apparatus during an operation of the apparatus.

According to another aspect, the present invention is directed to a system comprising: a tissue interface member suitable for positioning on the surface of the tissue; a tissue breaching apparatus that mates with the tissue interface member to achieve a desired alignment with the surface of the tissue; and a sensor device capable of mating to the tissue interface member when the tissue breaching device is not mated to the tissue interface member to achieve alignment with an ablated site of the tissue, wherein the sensor device detects a characteristic of a biological fluid collected from the ablated site of the tissue. The tissue breaching device may be any device that mechanically breaches the tissue, a heatable element device that thermally ablates the tissue, and an energy emitter device capable of emitting energy that is directly absorbed by the tissue. Alternatively, the tissue breaching device cooperates with an energy emitter device that cooperates with an energy absorbing layer positioned on, or a part of, the tissue interface member.

Similarly, the present invention is directed to method for detecting a characteristic of a biological tissue, comprising the steps of: placing a tissue interface member at a desired position onto the surface of the tissue; mating a tissue breaching apparatus to the tissue interface member to achieve alignment with the surface of the tissue; activating the tissue breaching apparatus; detaching the tissue breaching apparatus from the tissue interface member; and mating a sensor device to the tissue interface member to achieve alignment with a breached tissue site.

The present invention also is directed to a sensor device for sensing a characteristic of a biological fluid collected from a tissue, comprising: a housing; at least one opening in the housing to collect biological fluid from the tissue; at least one alignment member suitable for mating with a complementary alignment member of a tissue interface member positioned on a surface of the tissue for aligning the at least one opening in the housing with a predetermined surface portion of the tissue.

Similarly, the present invention is directed to an energy emitter apparatus comprising: an energy source for emitting energy suitable for absorption by an energy absorbing layer positioned in substantial contact with a surface of a tissue; and at least one alignment member suitable for mating with at least one complementary alignment member of a tissue interface member positioned on a surface of the tissue for aligning the energy emitted by the energy source with the energy absorbing layer.

The above description is intended by way of example only.

We claim:

1. A system comprising an alignment device for aligning at least one apparatus with respect to a surface of a tissue, the alignment device comprising a tissue interface member suitable for positioning on the surface of the tissue and mating with the apparatus to maintain alignment of the apparatus during an operation of the apparatus, the alignment device further comprising a removable energy absorbing layer attached to the tissue interface member, wherein the energy absorbing layer is responsive to energy directed thereon to heat up and to conductively transfer heat to the surface of the tissue to ablate the tissue to cause tissue ablation, and wherein the apparatus is an energy emitter apparatus including at least one energy source for emitting energy, wherein the energy emitter apparatus includes at least one alignment member that mates with the tissue interface member to achieve alignment with the tissue, so that, when the heat is transferred to the tissue, the layer may be removed to expose the ablated tissue.

2. The system of claim 1, wherein the energy absorbing layer further comprises a first and a second side, wherein the second side comprises adhesive material disposed thereon for adhering to the surface of the tissue.

3. The system of claim 1, wherein the alignment device has an inner periphery, wherein the energy absorbing layer includes a separation line adjacent the periphery, and wherein the energy absorbing layer is removable from the tissue interface member after tissue ablation.

4. The system of claim 1, wherein the tissue interface member mates with a first apparatus that emits energy to the energy absorbing layer to cause tissue ablation and with a second apparatus suitable for detecting a characteristic in a fluid collected from the tissue.

5. The system of claim 1, wherein the tissue interface member comprises of at least one clip that mates with a surface on the apparatus to hold the apparatus with respect to the tisáue interface member.

6. The system of claim 5, wherein the clip is biased to hold the first apparatus and second apparatus under tension.

7. The system of claim 1, wherein the tissue interface member has an exterior and an interior surface.

8. The system of claim 7, wherein interior surfaces of the tissue interface member engage with surfaces of the apparatus to align the apparatus with the tissue interface member.

9. The system of claim 7, wherein the exterior surfaces of the tissue interface member engage with surfaces of the apparatus to align the apparatus with the tissue interface member.

10. The system of claim 7, wherein the tissue interface member comprises a male alignment member or a female alignment member that mates with a complementary female alignment member or a male alignment member, respectively, on the apparatus.

11. The system of claim 1, wherein the tissue interface member comprises at least one magnetic surface portion to mate with at least one complementary magnetic surface portion on the apparatus.

12. The system of claim 1, wherein the tissue interface member comprises a threaded member that mates with a complementary threaded member on the apparatus.

13. The system of claim 1, wherein the tissue interface member further comprises an adhesive element allowing the device to be attached to the surface of tissue to maintain alignment of the apparatus with respect to the surface of the tissue.

14. The system of claim 1, wherein the tissue interface member comprises a strap that extends around a body portion of a user to mount and hold the tissue interface member to the surface of the tissue at a desired position to maintain the alignment of the apparatus with respect to the surface of the tissue.

15. The system of claim 1, further comprising a sensor to detect a characteristic of a biological fluid collected from the tissue, wherein the sensor comprises at least one alignment element that mates with the tissue interface member to achieve alignment of the sensor over a portion of the ablated tissue.

16. The system of claim 1, wherein the energy emitter apparatus further comprises a controller and a sensor coupled to the controller, wherein the sensor detects when the energy emitter apparatus is in position on the tissue interface member, and wherein the controller is responsive to the sensor to enable activation of the energy emitter apparatus.

17. The system of claim 16, wherein the sensor on the energy emitter apparatus comprises a pressure sensor responsive to sufficient pressure from engagement with the tissue interface member.

18. The system of claim 17, wherein the energy emitter apparatus further comprises a switch that is closed by an element on the tissue interface member when the energy emitter apparatus is properly installed in the tissue interface member, wherein the controller of the energy emitter apparatus is responsive both to the switch being closed and the pressure sensor detecting sufficient pressure to enable activation of the energy emitter apparatus.

19. In combination, the system of claim 1, and a tissue breaching device for mechanically breaching the tissue and forming at least one opening therein, wherein the tissue breaching device comprises at least one alignment member that mates with the tissue interface member to achieve alignment with the tissue.

20. In combination, the system of claim 1, and a tissue breaching device comprising a heatable element for breaching the surface of the tissue by thermally ablating the tissue to form at least one opening therein, wherein the tissue breaching device comprises at least one alignment member that mates with the tissue interface member to achieve alignment with the tissue.

21. The system of claim 1, wherein the at least one apparatus comprises a substance delivery device constructed and arranged for delivery of a substance to the ablated tissue, wherein the substance delivery device comprises at least one alignment element that mates with the tissue interface member to achieve alignment of the substance delivery device over a portion of the ablated tissue.

22. The system of claim 21, wherein the substance delivery device further comprises a controller and a sensor coupled to the controller, wherein the sensor detects when the substance delivery device is in position on the tissue interface member, and wherein the controller is responsive to the sensor to enable activation of the substance delivery device.

23. The system of claim 22, wherein the sensor on the substance delivery device comprises a pressure sensor responsive to sufficient pressure from engagement with the tissue interface member.

24. The system of claim 23, wherein the substance delivery device further comprises a switch that is closed by an element on the tissue interface member when the substance delivery device is properly installed in the tissue interface member, wherein the controller of the substance delivery device is responsive both to the switch being closed and the pressure sensor detecting sufficient pressure to enable activation of the substance delivery device.

25. A system comprising:
a tissue interface member suitable for positioning on the surface of the tissue;
a tissue breaching device that mates with the tissue interface member to achieve a desired alignment with the surface of the tissue, wherein the tissue breaching apparatus forms at least one opening in the tissue; and
a sensor device capable of mating to the tissue interface member when the tissue breaching device is not mated to the tissue interface member so that the sensor device is aligned with the at least one opening to achieve alignment with an ablated site of the tissue, wherein the sensor device collects a biological fluid by the force of a pressure differential between the at least one opening and sensor device, and wherein the sensor device detects a characteristic of a biological fluid collected from the at least one opening in the tissue; and, wherein the tissue breaching device is capable of mating to the tissue interface member to achieve alignment and is selected from a group comprising of a device that mechanically breaches the tissue, a heatable element device that thermally ablates the tissue, and an energy emitter device capable of emitting energy that is directly absorbed by the tissue and;

wherein the system further comprising an energy absorbing layer attached to the tissue interface member, wherein the energy absorbing layer is responsive to energy directed thereon to heat up and to conductively transfer heat to the surface of the tissue to ablate the tissue, and wherein the tissue breaching device comprises the energy emitter device comprising at least one energy source for emitting energy to the energy absorbing layer.

26. The system of claim 25, wherein the energy absorbing layer is removable from the tissue interface member.

27. The system of claim 25, wherein the energy absorbing layer comprises an adhesive on one surface thereof attachable at a desired location proximate to the surface of the tissue.

28. The system of claim 27, wherein the energy absorbing layer is simultaneously removed upon detachment of the tissue breaching apparatus.

29. The system of claim 25, wherein the sensor device draws biological fluid from the at least one opening under a suction force.

30. A method for detecting a characteristic of a biological tissue, comprising the steps of:
  placing a tissue interface member at a desired position onto the surface of the tissue;
  mating a tissue breaching apparatus to the tissue interface member to achieve alignment with the surface of the tissue;
  activating the tissue breaching apparatus to form a breached tissue site;
  detaching the tissue breaching apparatus from the tissue interface member;
  positioning an energy absorbing layer proximate to the surface of the tissue in alignment with the tissue interface member;
  removing the energy absorbing layer; and
mating a sensor device to the tissue interface member to achieve alignment with the breached tissue site.

31. The method of claim 30, wherein the step of activating a tissue breaching device involves activating the device selected from a group comprising a mechanical device, an electrically heatable element device, or an energy emitter device.

32. The method of claim 31, wherein the step of activating the energy emitter device further comprises;
  mating an energy emitter device to the tissue interface member to achieve alignment with the energy absorbing layer;
  activating the energy emitter device to emit energy to the energy absorbing layer, wherein the energy absorbing layer is responsive to energy directed thereon to heat and conductively transfer heat to the surface of the tissue thereby ablating the tissue;
  detaching the energy emitter device from the tissue interface member; and
  simultaneously removing the energy absorbing layer as the energy emitter device is detached.

33. The method of claim 32, and wherein the step of placing the tissue interface member on the tissue is performed with the energy absorbing layer attached in a desired alignment to the tissue interface member.

34. The method of claim 32, and further comprising the step of removing the energy absorbing layer from the tissue interface member after the tissue is ablated.

35. The method of claim 32, and further comprising the step of simultaneously removing the energy absorbing layer from the tissue interface member together with detachment of the energy emitter device from the tissue interface member.

36. The method of claim 31, wherein the step of activating the energy emitter device causes the formation of at least one opening in the tissue.

37. The method of claim 36, and further comprising the step of detecting a characteristic of a biological fluid collected from the at least one opening in the tissue with the sensor device.

38. The method of claim 37, wherein the step of positioning the energy absorbing layer comprises adhering the energy absorbing layer to the tissue with an adhesive.

39. A system comprising an alignment device for aligning a energy emitter apparatus with respect to a surface of a tissue, the alignment device comprising a tissue interface member suitable for positioning on the surface of the tissue and mating with the energy emitter apparatus to maintain alignment of the energy emitter apparatus during an operation of the energy emitter apparatus, the alignment device further comprising a removable energy absorbing layer attached to the tissue interface member, wherein the energy absorbing layer is responsive to energy directed thereon to heat up and to conductively transfer heat to the surface of the tissue to ablate at least a portion of the tissue, wherein the energy emitter apparatus comprises at least one energy source for emitting energy and at least one alignment member that mates with the tissue interface member to achieve alignment with the tissue, and wherein, when heat is transferred to the tissue, the energy absorbing layer may be removed to expose the portion of the tissue that is abalated.

40. A system for poration and alignment comprising:
  an energy emitter apparatus including at least one energy source for emitting energy; and
  a tissue interface member suitable for positioning on a surface of a tissue and mating with the energy emitter apparatus to maintain alignment of the energy emitter apparatus with respect to the surface of the tissue during operation of the energy emitter apparatus;
  wherein the energy emitter apparatus comprises at least one alignment member that mates with the tissue interface member to achieve alignment with the tissue and wherein the energy emitter apparatus further comprises a controller and a sensor coupled to the controller, wherein the sensor detects when the energy absorbing apparatus is in position on the tissue interface member, wherein the controller is responsive to the sensor to enable activation of the energy emitter apparatus, wherein the sensor on the energy emitter apparatus includes a pressure sensor responsive to sufficient pressure from engagement with the tissue interface member, wherein the energy emitter apparatus further comprises a switch that is closed by an element on the tissue interface member when the energy emitter apparatus is properly installed in the tissue interface member, and wherein the controller of the energy emitter apparatus is responsive both to the switch being closed and the pressure sensor detecting sufficient pressure to enable activation of the energy emitter apparatus.

41. A system comprising:

a tissue interface member suitable for positioning on a surface of a tissue;

a tissue breaching device that mates with the tissue interface member to achieve a desired alignment with the surface of the tissue, wherein the tissue breaching device is capable of mating to the tissue interface member to achieve alignment and comprises an energy emitter device capable of emitting energy that is directly absorbed by the tissue;

a sensor device capable of mating to the tissue interface member when the tissue breaching device is not mated to the tissue interface member to achieve alignment with an ablated site of the tissue, wherein the sensor device detects a characteristic of a biological fluid collected from the ablated site of the tissue; and an energy absorbing layer attached to the tissue interface member, wherein the energy absorbing layer is responsive to energy directed thereon to heat up and to conductively transfer heat to the surface of the tissue to ablate the tissue;

wherein the energy emitter device comprises at least one energy source for emitting energy to the energy absorbing layer.

42. A method for detecting a characteristic of a biological tissue, comprising: placing a tissue interface member at a desired position onto a surface of a tissue;

positioning an energy absorbing layer proximate to the surface of the tissue in alignment with the tissue interface member;

mating a tissue breaching apparatus to the tissue interface member to achieve alignment with the surface of the tissue and the energy absorbing layer, the tissue breaching apparatus comprising an energy emitting device;

activating the tissue breaching device to emit energy to the energy absorbing layer, wherein the energy absorbing layer is responsive to energy directed thereon to heat and conductively transfer heat to the surface of the tissue thereby ablating the tissue;

detaching the tissue breaching apparatus from the tissue interface member; removing the energy absorbing layer; and mating a sensor device to the tissue interface member to achieve alignment with a breached tissue site.

* * * * *